(12) United States Patent
Schneider et al.

(10) Patent No.: US 8,246,649 B2
(45) Date of Patent: Aug. 21, 2012

(54) ELECTROSTATIC VASCULAR FILTERS

(76) Inventors: M. Bret Schneider, Portola Valley, CA (US); Rogelio Moncada, New Orleans, LA (US)

(*) Notice: Subject to any disclaimer, the term of this patent is extended or adjusted under 35 U.S.C. 154(b) by 130 days.

(21) Appl. No.: 12/383,094

(22) Filed: Mar. 18, 2009

(65) Prior Publication Data

US 2009/0248060 A1    Oct. 1, 2009

Related U.S. Application Data

(60) Provisional application No. 61/037,983, filed on Mar. 19, 2008.

(51) Int. Cl.
*A61M 29/00* (2006.01)

(52) U.S. Cl. ........................... 606/200

(58) Field of Classification Search .............. 606/200, 606/159, 1, 7, 14, 198; 623/1.11, 2.11, 23.72; 604/104–107
See application file for complete search history.

(56) References Cited

U.S. PATENT DOCUMENTS

| | | | | | |
|---|---|---|---|---|---|
| 5,314,424 | A | * | 5/1994 | Nicholas | 606/41 |
| 5,935,303 | A | * | 8/1999 | Kimura | 96/69 |
| 6,068,645 | A | * | 5/2000 | Tu | 606/200 |
| 6,989,027 | B2 | * | 1/2006 | Allen et al. | 623/2.18 |
| 7,220,271 | B2 | * | 5/2007 | Clubb et al. | 606/200 |
| 2001/0039431 | A1 | * | 11/2001 | DeVries et al. | 606/200 |
| 2002/0161394 | A1 | * | 10/2002 | Macoviak et al. | 606/200 |
| 2003/0109897 | A1 | * | 6/2003 | Walak et al. | 606/200 |
| 2003/0130682 | A1 | * | 7/2003 | Broome et al. | 606/200 |
| 2003/0176888 | A1 | * | 9/2003 | O'Connell | 606/200 |
| 2004/0102806 | A1 | * | 5/2004 | Broome et al. | 606/200 |
| 2004/0158275 | A1 | * | 8/2004 | Crank et al. | 606/200 |
| 2006/0030876 | A1 | * | 2/2006 | Peacock et al. | 606/200 |
| 2006/0058832 | A1 | * | 3/2006 | Melzer et al. | 606/200 |
| 2006/0178695 | A1 | * | 8/2006 | Decant et al. | 606/200 |
| 2006/0184193 | A1 | * | 8/2006 | Lowe et al. | 606/200 |
| 2006/0229658 | A1 | * | 10/2006 | Stivland | 606/200 |
| 2009/0062840 | A1 | * | 3/2009 | Angel | 606/200 |
| 2009/0112228 | A1 | * | 4/2009 | Deshpande et al. | 606/128 |

OTHER PUBLICATIONS

De Vries, AJ et al., The rationale for fat filtration during cardiac surgery, Perfusion 2002; 17:29-33.
De Vries, AJ et al., Clinical evaluation of a new fat removal filter during cardiac surgery, European J. of Cardio-thoracic Surgery 2004 25:261-266.
Bruil, A, Poly(ethyleneimine) modified filters for the removal of leukocytes from blood, J. of Biomedical Materials Research 1993 27:1253-1268.
Mohanty, K, The Effect of a Venous Filter on the Embolic Load During Medullary Canal Pressurization:, J. of Bone and Joint Surgery 2005 87:1332.
Ramirez, G, Detection and removal of fat particles from postoperative salvaged blood in orthopedic surgery, Transfusion 2002 42:66-75.
Kiely, LJ, Estimate of Non electrostatic Interaction Free Energy Parameters for Milk Fat Globules, J. Dairy Sci. 2003 86:3110-3112.

* cited by examiner

*Primary Examiner* — Gary Jackson
*Assistant Examiner* — Christopher Schubert
(74) *Attorney, Agent, or Firm* — Kilpatrick Townsend & Stockton LLP

(57) ABSTRACT

An intravascular filter is constructed to electrostatically capture and retain particles of a targeted type (for example fat or methacrylate emboli), even if those particles are physically small enough to slip through the filter in the absence of electrostatic attraction. Specific types of targeted particles are thereby captured and retained with improved efficiency, while permitting free flow of non-targeted particles. This improvement permits intravascular filters to be constructed with low-resistance, widely spaced filter elements. Accordingly, more targeted particles are captured, less thrombosis occurs, less pressure drop occurs across the filter, and perfusion or blood collection in downstream areas is maintained.

21 Claims, 4 Drawing Sheets

ELECTROSTATIC VASCULAR FILTERS

RELATED APPLICATIONS

This application is related to and claims the benefit of the priority date of U.S. Provisional Patent Application Ser. No. 61/037,983, by M. Bret Schneider and Rogelio Moncada, titled "Electrostatic Vascular Filter", filed Mar. 19, 2008. The foregoing referenced application is hereby incorporated as though set forth in its entirety herein.

FIELD OF THE INVENTION

The invention described herein relates to medical devices and methods of use thereof. More particularly, the invention relates to a retrievable intravascular filter and methods for filtering embolic material within a vessel of a subject.

REFERENCES

Berger, US Patent Application Publication No. US2007/0225644 A1, Embolic Removal for Orthopedic Procedures, Sep. 27, 2007.

Clubb et al., U.S. Pat. No. 7,220,271 B2, Embolic Filters Having Multiple Layers and Controlled Pore Size.

McGuckin et al., U.S. Pat. No. 6,623,506, Vein Filter.

Sutton, U.S. Pat. No. 7,229,462, Vascular Filter System for Carotid Endarterectomy Kimmell, U.S. Pat. No. 3,952,747, Filter and Filter Insertion Element Kimura, U.S. Pat. No. 5,935,303, Electrostatic Filter Ye et al., U.S. Pat. No. 6,241,999, Method for Producing Liposomes with Increased Percent of Compound Encapsulated.

Rousseau H, Perreault P, Otal P, Stockx L, Golzarian J, Oliva V, Reynaud P, Raat F, Szatmari F, Santoro G, Emanuelli G, Nonent M, Hoogeveen Y. The 6-F nitinol TrapEase inferior vena cava filter: results of a prospective multicenter trial. J Vasc Interv Radiol. 2001 March; 12(3):299-304.

Men'shikova Y A, Evseeva T G, Chekina N A, Peretolchin M V, Skurkis Y O, Ivanchev S S. Synthesis of Monodisperse Polymethyl Methacrylate particles in Buffered Solutions under the Action of Carboxyl-Containing Initiator. Russian Journal of Applied Chemistry, Vol. 75, No 12, 2002 pp 1993-1998

A J de Vries, Y J Gu and W van Oeveren. The rationale for fat filtration during cardiac surgery. Perfusion 2002; 17; 29

De Vries A J, Gu J Y, Douglas Y L, Post W J, Lip H, Oeveren W V. Clinical evaluation of a new fat removal filter during cardiac surgery. European Journal of Cardio-thoracic Surgery. 25 (2004) 261-266

Ramirez G, Romero A, Garcia-Vallejo J J, Munoz M. Detection and removal of fat particles from postoperative salvaged blood in orthopaedic surgery. Transfusion. 2002; 42:66-75

Taviloglu K, Yanar H. Fat embolism syndrome. Surg Today. 2007; 37(1):5-8. Epub 2007

Xiong Y L, Noel C, Moody W G Journal of Food Science: Textural and Sensory Properties of Low-Fat Beef Sausages with Added Water and Polysaccharides as Affected by pH and Salt. Journal of Food Science 64 (3), 550-554

Peng M, Li D, Chen Y, Zheng Q. TI: Electrostatic-Assembly of Carbon Nanotubes (CNTs) and Polymer Particles in Water: a Facile Approach to Improve the Dispersion of CNTs in Thermoplastics. Macromolecular Rapid Communications. Vol 27, No. 11, p 859-864 2006

Kiely L J, Olson N F. Estimate of Non-Electrostatic Interaction Free Energy Parameters for Milk Fat Globules. J. Dairy Sci. 86:3110-3112 (2003)

Adrianus J. de Vries A J, Gu Y J, Douglas Y L, Post W J, Lip H, van Oeveren W. Clinical evaluation of a new fat removal filter during cardiac surgery European Journal of Cardio-Thoracic Surgery Volume 25, Issue 2, February 2004, Pages 261-266

Taviloglu K, Yanar H. Fat Embolism Syndrome. Surgery Today. 2007. 37:5-8

Steinbeck M. J., Robinson J. M, Karnovsky M. J. Activation of the neutrophil NADPH-oxidase by free fatty acids requires the ionized carboxyl group and partitioning into membrane lipid. J Leukoc Biol. 1991 April; 49(4):360-8

Mastraneglo A. M., Jeitner T. M., Eaton J. W. Oleic acid increases cell surface expression and activity of CD 11b on human neutrophils. J Immunol. 1998 Oct. 15; 161 (8): 4268-75

Cnop M., Hannaert J. C., Pipeleers D. G. Troglitazone does not protect rat pancreatic beta cells against free fatty acid-induced cytotoxicity. Biochem Pharmacol. 2002 Apr. 1; 63(7): 1281-5.

Kamijo A., Kimura K., Sugaya T, Yamanaouchi M, Hase H, Kaneko T, Hirata Y, Goto A., Fujita T., Omata M. Urinary free fatty acids bound to albumin aggravate tubulointerstitial damage. Kidney Int. 2002 November; 62(5):1628-37

Grotjohan H. P., van der Heijde R. M., Jansen J. R., Wagenvoort C. A., Versprille A. A stable model of respiratory distress by small injections of oleic acid in pigs. Intensive Care Med. 1996 April; 22(4):336-44

BACKGROUND OF THE INVENTION

Fat and Fat Embolism

Lipids may be classified as either "anionic" (e.g. most phospholipids), "cationic" (e.g. milk fat globules (Kiely and Olson 2003)), or "neutral". Human fat tissue is an example of a lipid which in its living, unperturbed form, is electrically neutral. But once it is surgically or metabolically disrupted, human fat begins a breakdown into several lipid fractions, some positive, some negative, and some neutral. For example, free fatty acids (FFAs) are highly polarized molecules (de Vries et al 2004). The trans form free fatty acids (FFAs) carry a negative charge (Steinbeck et al 1991). FFAs are particularly harmful in the circulation. FFAs cause vasoconstriction and granulocytes activation through surface expression and activity of CD11b (Mastraneglo et al 1998). FFAs have been implicated in b-cell damage in the pancreas (Cnop et al 2002), tubulointerstitial damage in the kidney (Kamijo et al 2002), and acute respiratory distress syndrome in the lungs (Grotjohan et al 1996). Fortunately, because a FFA molecule is a highly polarized structure, filtration as a means to remove FFAs from the blood stream holds some promise. In fact, extracorporeal, (i.e., outside the human body) mechanical blood filtration targeting fat has been demonstrated in blood from orthopedic patients (Ramirez et al 2002). Similar extracorporeal mechanical filtration during cardiac surgery has shown that FFAs are retained by the filter particularly well, a phenomenon that is thought likely to be related to the polarity of the FFA molecule (de Vries et al 2004).

The embolization of fat particles into organs including the lung and brain is an important cause of medical morbidity, particularly following orthopedic trauma. When a bone is fractured, there is usually some fat released into the venous circulation. These particles are distributed downstream, particularly into the lung, but in most cases do not cause an obvious medical syndrome. Following orthopedic surgical procedures, however, the escaped fat particle load becomes very large, and a fat embolism syndrome may occur in a third of patients undergoing these procedures. Symptoms may range from mild respiratory distress with skin and eye symptoms, to severe pulmonary edema and death (Taviloglu et. al. 2007).

Methacrylate and Methacrylate Embolism

Methacrylate is frequently used in orthopedic surgery to affix implants and to remodel lost bone. Methyl methacrylate (MMA) polymerizes and thereby hardens into polymethyl methacrylate (PMMA). The polymer PMMA is a lipophilic molecule of varying chain length, with the molecular formula $(C_5O_2H_8)n$. It is sold under a variety of medical and non-medical trade-names including the familiar "Plexiglas". The two hydroxyl groups carry a negative electrostatic propensity, while the hydrogens impart positive charges. Consequently, the molecule has intrinsic electrostatic properties which become manifest under various polymerization and ambient pH conditions. Additionally, methacrylate molecules may be purposefully made to bear either a positive or a negative charge by means known in the art. For example, Peng et al. describe "a facile and organic-solvent-free method" involving the production of positively charged PMMA by emulsion polymerization, in which a cationic element such as the monomer methacryloyloxyethyltrimethylammonium chloride (METAC) is copolymerized with methacrylate. Likewise, negatively charged PMMA is produced using anionic comonomer sodium 2-acrylamido-2-methylpropanesulphonate (NaAMPS) (Peng et al. 2006). Particles of these materials, however, are frequently taken away from the operative site by nearby veins. When the particles are brought into the fine capillaries of the lung or other regions of the body, circulatory blockages and tissue damage may result.

Intravascular Filter Usage and Design Considerations

The engineering of vascular filters is complicated by the need to make the particle-capturing mesh tight enough to capture the targeted particles, but not so tight so as to impede circulation, or otherwise cause thrombus formation on the mesh. An excessively loose mesh (in which the spaces between the filter elements are too distant) results in failure to capture smaller emboli. Conversely, a mesh that is too tight (in which filter elements are too close to one another) increases the resistance to blood flow, and may trap particles indiscriminately, leading to early thrombosis and occlusion of paths through the filter.

Electrostatic Filters

Electrostatic filters are known principally for use in water filtration, cleaning of fabric, air/allergen filtration, and in food processing, but have not been adapted to the unique environment and demands of intravascular use.

It would be desirable to have a venous filter capable of capturing small embolic particles, including the most dangerous fatty acids, without attracting platelets and promoting thrombosis. It would also be desirable to deploy such a filter via a catheter prior to a high-embolic-risk procedure, and to be able to retrieve it at the conclusion of that procedure.

The invention set forth herein relates to a retrievable protective mesh which is inserted into a blood vessel which is deemed at risk for delivering potentially harmful embolic particles to distal organs. This mesh is deployed via catheter, or by direct cut-down into the vein, and is of sufficient patency to allow normal blood cells and small clumps of cellular material through. In particular, this intravascular filter is constructed to employ electrostatic forces in a manner that permits adhesive forces to capture particles of the targeted type (for example fat or methacrylate emboli), and to retain these particles, even those which might otherwise be physically small enough to slip through the filter. Specific types of targeted particles are thereby captured and retained with improved efficiency, permitting filter elements to be more widely spaced than would otherwise be necessary, thereby decreasing both resistance and the propensity for thrombosis. The device is designed to be retrieved post-op, and the accumulated debris on the mesh analyzed in the laboratory. The device provides protection from embolism and stroke resulting from debris released by sites of tissue trauma. The device provides protection from embolism and stroke resulting from debris released by sites of tissue trauma.

SUMMARY OF THE INVENTION

A filter system for removal of embolic particles from a blood vessel of a subject is disclosed, where the system has a filtration element deployable within a blood vessel of the subject. At least a portion of the filtration element is electrically conductive, and either an anode or a cathode is in electrical communication with the filtration element. Embolic particles carrying an electrostatic charge opposite that of said anode or said cathode are attracted to the filtration element. The embolic particles may be lipids or methacrylate. The filtration element may further comprise a mesh, one or more struts, and/or one or more purse strings. The system may be constructed to entrap emboli and/or embolic material, some of which may comprise a diameter of 10 microns.

The filter system may further comprise a delivery configuration and a deployed configuration whereby said system may be delivered and deployed in a minimally invasive percutaneous manner. The system may also be retrieved from the vessel of a subject in a minimally invasive percutaneous manner.

DETAILED DESCRIPTION OF THE INVENTION

Figures 1A, 1B:
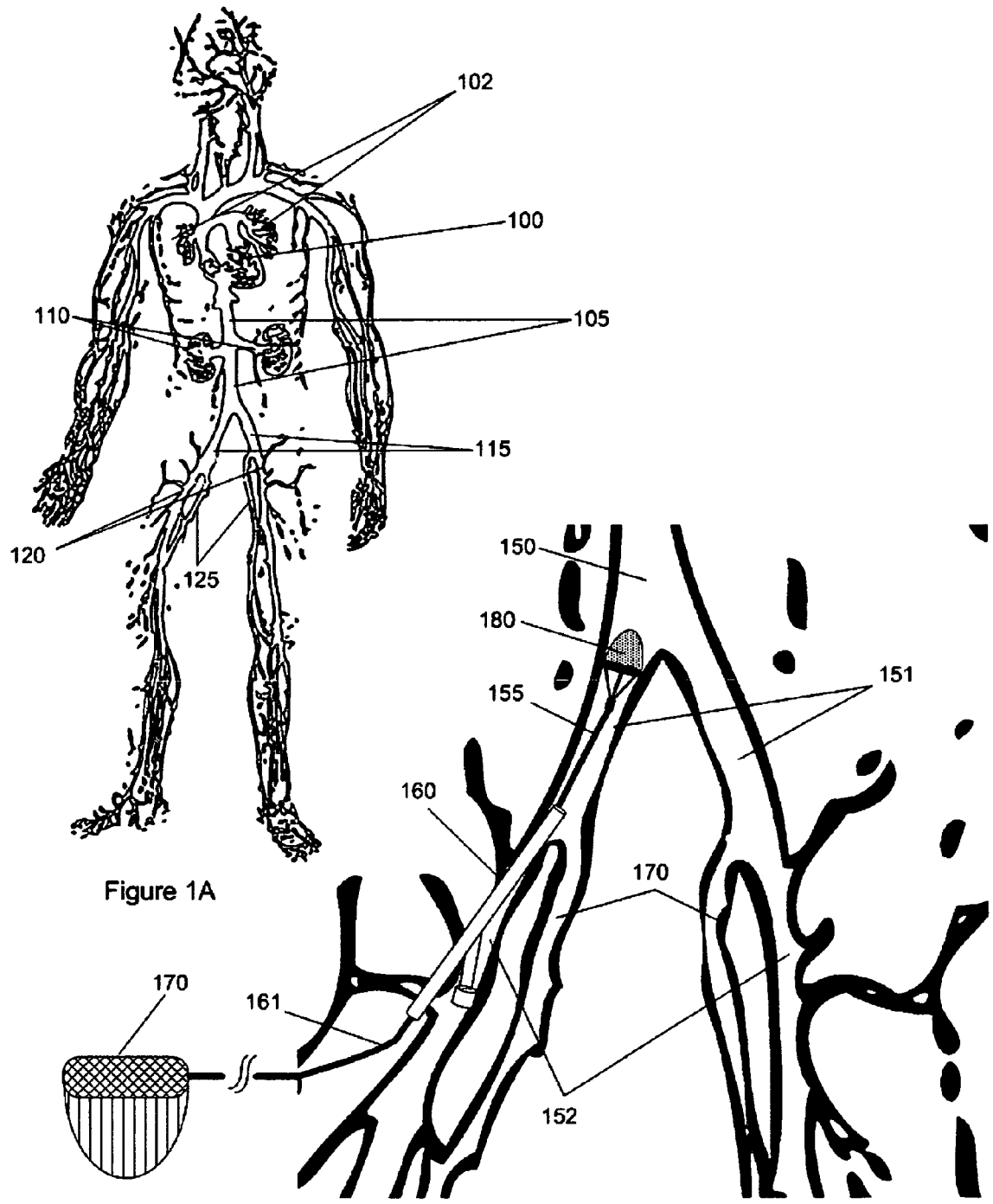
FIG. 1A illustrates the venous systems of the body, which along with arteries, arterioles, venules and capillaries, constitute the vascular system.
FIG. 1B illustrates a plan view of one embodiment according to the invention in use as it is inserted into the right femoral vein of a subject, the right femoral vein shown in "see-through" mode, and a portion of the invention illustrated schematically.

FIG. 1A illustrates the major anatomical aspects of the human venous system. Via this natural system, deoxygenated blood is returned to heart 100 via inferior vena cava 105, and oxygenated blood via pulmonary veins 102. Below renal veins 110, inferior vena cava 105 emerges from the convergence of the left and right common iliac veins 115. Femoral veins 120 emerge upstream (distally) from the common iliac veins 115, and long saphenous veins 125 also arise in this region.

As shown in FIG. 1B, each of the common iliac veins 151 arises from the confluence of the femoral veins 152 and the long saphenous veins 170. Interventional catheter 155 may be placed into this system through femoral vein 152, for example through the lumen of guide catheter 160 which may contain electrically conductive wires 161. Through the lumen, catheter 155 may advance to, for example, the common iliac artery, and may deploy filter mechanism 180. Distal end of catheter 155 may be used to deploy and to retrieve filtration device 180 as will be described in the pages to follow. Conductive wires 161 within interventional catheter 155 are in electrical communication with power unit 170.

Figure 2A:
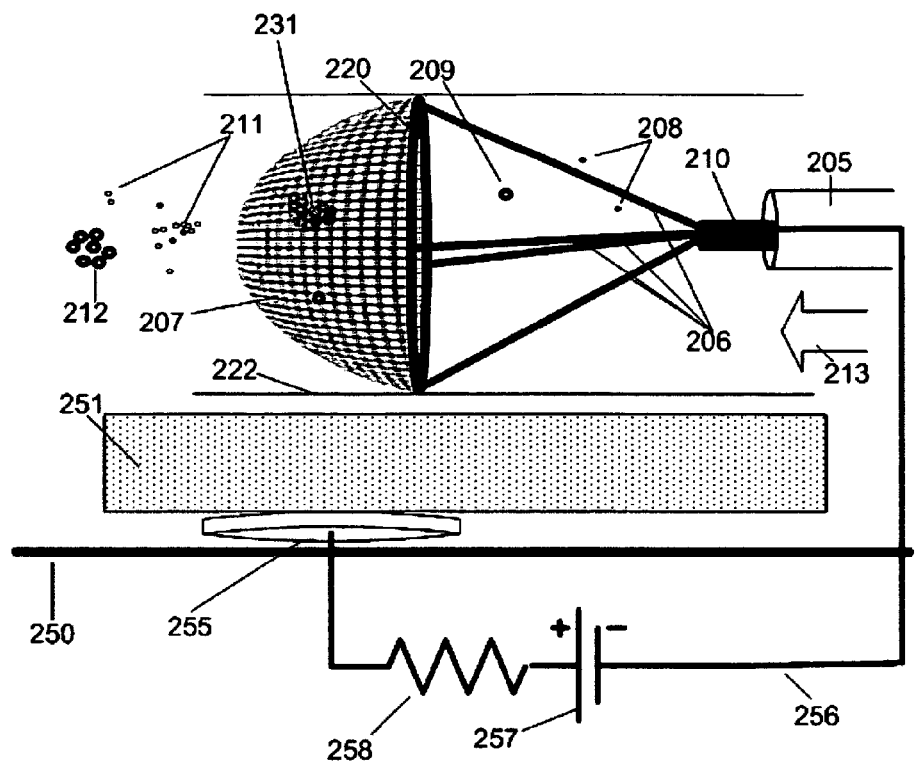
FIG. 2A illustrates one embodiment according to the invention in a side view and partial schematic as it is deployed in a vessel of a subject, the vessel and attendant structures shown in cross-section.
Figure 2B:
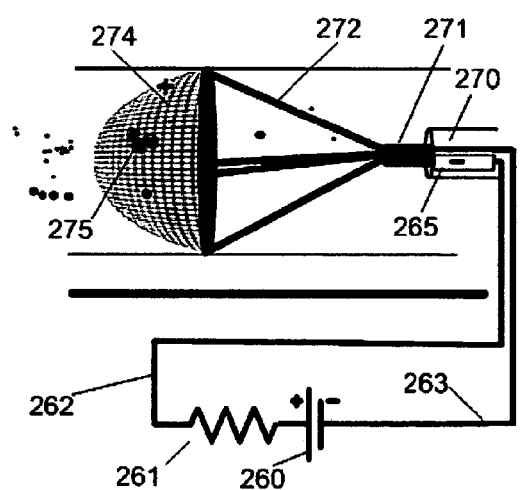
FIG. 2B illustrates an alternative embodiment according to the invention in a side view and partial schematic as it is deployed in a vessel of a subject, the vessel and attendant structures shown in cross-section.
Figure 2C:
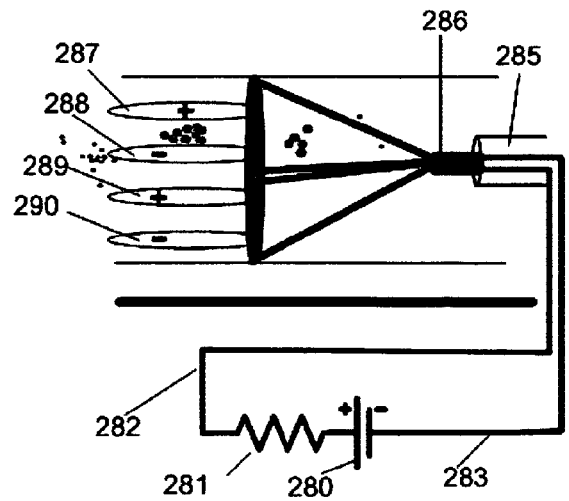
FIG. 2C illustrates yet another embodiment according to the invention in a side view and partial schematic as it is deployed in a vessel of a subject, the vessel and attendant structures shown in cross-section.

FIGS. 2A, 2B and 2C illustrate use of electrostatic charges imparted upon an electrically conductive filtration mesh in order to repel platelets and red blood cells, and to attract particles and other cells and materials bearing a net positive electrostatic charge. In FIG. 2A, battery 257 has a negative pole connected to wire 256, which runs through the core of interventional catheter 210, and through struts 206, which create a conductive contact with perimeter ring 220 and mesh 207. The positive pole of battery 257 has resister 258 and is attached to an internal or external surface 250 of the body of the patient via electrode 255. Endogenous insulating tissue 251 generally lies between the vein walls 222 and electrode 255. As a result of this arrangement, a net negative charge may be imparted upon filter mesh 207. This results in the trapping of electropositive particles, such as electropositively polymerized methacrylate 231, but not in the entrapment of electronegative particles such as platelets and red blood cells. Struts 206, perimeter ring 220 and mesh 207 may be made of conductive materials including, for example, stainless steel, titanium and chromium or nitinol. Blood flow is shown in this embodiment in direction 213, although the principles apply to either flow direction. In an alternative embodiment, the opposite polarity is used, in which the filtration bears a positive charge and serves to attract negatively-charged particles, for example, electronegative fat components or methacrylate that has been prepared with an anionic polymerization compound. Methods are known in the art for imparting electrostatic charges on plastics, for example using techniques similar to those described by Peng et al 2006. Positively charged methacrylate may be prepared by emulsion polymerization, in which cationic element such as monomer methacryloyloxyethyltrimethylammonium chloride (METAC) is copolymerized with methacrylate. Alternatively, negatively charged PMMA may be produced using an anionic comonomer such as sodium 2-acrylamido-2-methylpropanesulphonate (NaAMPS). Such ionic copolymerization agents are non-toxic, and may alternatively be used to impart ionic charges on many thermoplastics, rubbery polymers, or their copolymers, including PMMA, polystyrene, polyacrylonitrile, and polybutadiene, and others.

In FIG. 2B, a similar configuration is shown, in which the positive pole is placed on filtration mesh 274, while the negative pole is placed upon the body of the guide catheter 265, thereby trapping electronegative particles 275. Alternatively, negative electrode 265 may be placed in another intravascular location, such as upon interventional catheter 271. FIG. 2C illustrates an embodiment in which filtration elements 287, 288, 289 and 290 are each imparted with either a negative or a positive charge. Filtration element 287 and 289 are positive, while filtration elements 288 and 290 are negative. Maintaining charge on each of these elements is accomplished by sending positive wire 282 and negative wire 283, which pass through interventional catheter 286, on the interior of guide catheter 285, and originate from battery 280, with positive wire 282 receiving current limited by resistor 281.

Figure 3A:
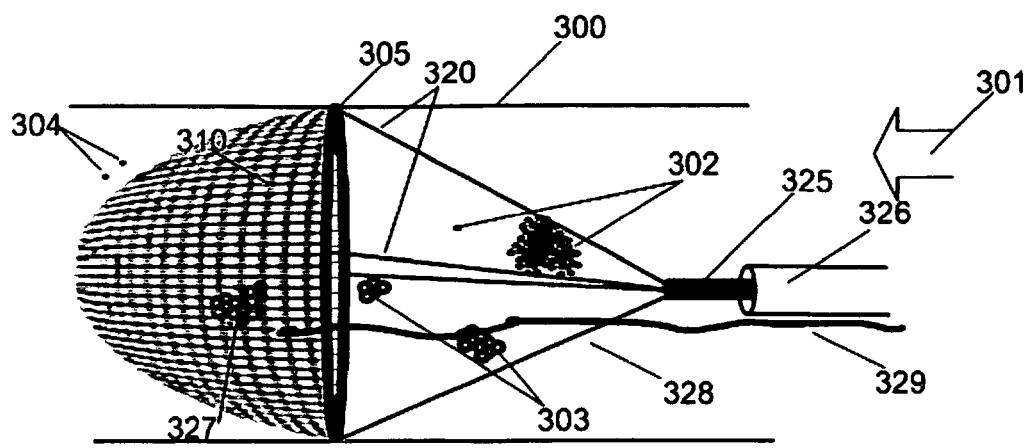
FIG. 3A shows an alternative embodiment according to the invention in a side view as it is deployed in a vessel of a subject, the vessel shown in cross-section.

FIG. 3A illustrates an embodiment of the present invention in which the filtration mesh 310 is deployed via guide catheter 326 and interventional catheter 325 from upstream of the targeted filtration site. Note direction of the blood flow 301. Red blood cells 302 are able to pass through mesh 310, as seen with red blood cells 304, while large materials such as methacrylate particles 303 are trapped within the mesh as methacrylate particles 327. The same principle applies for fat cells, which, like methacrylate, are larger than the red and white blood cells, and are trapped by a 20 micron or less vessel. Lumen margin 300, most often the endothelium of the vein in which the device is deployed, is shown with expansible lumen perimeter ring 305 fitting against lumen margin 300. Filtration mesh 310 is delivered by interventional catheter 325, which passes out from guide catheter 326, and is held in place by flexible, expansible lumen perimeter ring 305, which is held orthogonal to the flow of blood 301 by flexible cords 328. Perimeter ring 305 may be made of materials including, as an example, polytetrafluoroethylene (PTFE). Cords may be made of materials including for example PTFE, nylon, and suture materials including Vicryl. Filtration mesh 310 may have perforations of approximately 10 to 30 microns in size, so as to allow passage of endogeneous blood cells and very small clumps, but not of fat cells, nor of methacrylate particles. Mesh 310 may also be made of materials including nitinol. Purse string 329 serves to collapse perimeter ring 305, closing off mesh 310 to prevent escape of trapped particles as the device is received and removed from intravascular placement, typically at the end of a surgical procedure.

Figure 3B:
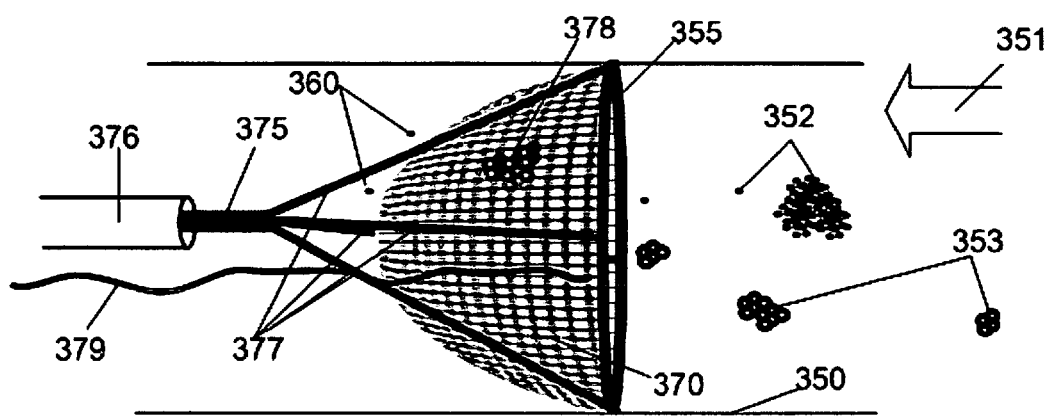
FIG. 3B shows an alternative embodiment according to the invention in a side view as it is deployed in a vessel of a subject, the vessel shown in cross-section.

FIG. 3B illustrates an embodiment of the present invention in which filtration mesh 370 is deployed via guide catheter 376 and interventional catheter 375 from downstream of the targeted filtration site, by virtue of semi-rigid struts 377 (instead of flexible cords as seen in FIG. 2A). Note direction of blood flow 351. Following deployment, filtration mesh 370, fixed upon expansible lumen perimeter ring 355, is held into an extended position by semi-rigid struts 377. At the convergence of struts 377, a latched or spring-actuated mechanism may be used to assist with the deployment and retrieval processes. The closure process may be facilitated via purse string 379.

Figure 3C:
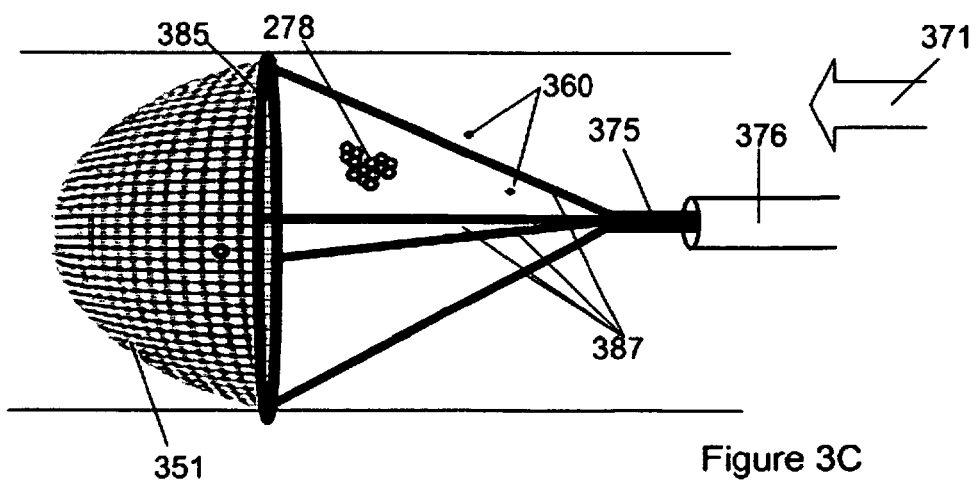
FIG. 3C shows an alternative embodiment according to the invention in a side view as it is deployed in a vessel of a subject, the vessel shown in cross-section.

FIG. 3C illustrates an embodiment of the present invention in which semi-rigid struts 387 are used when mesh 351 is deployed downstream of blood flow 371, (in a manner similar to that accomplished with flexible cords in FIG. 3A). Use of semi-rigid struts 387 can permit greater each of deployment and closure of perimeter ring 385 and mesh 351, optionally without need for a purse string.

Figure 4A:
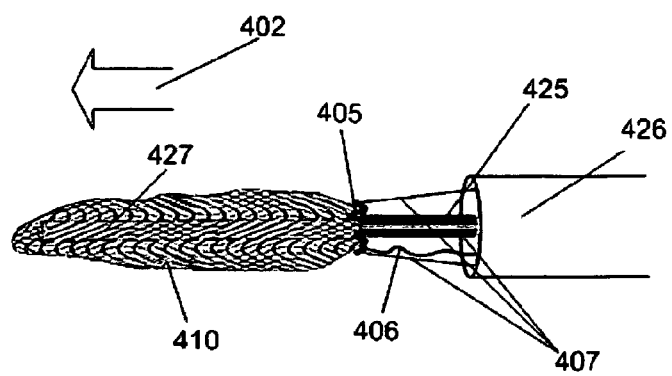
FIG. 4A illustrates an alternative embodiment according to the invention in a side view during a step of deployment in a vessel of a subject, the vessel shown in cross-section.
Figure 4B:
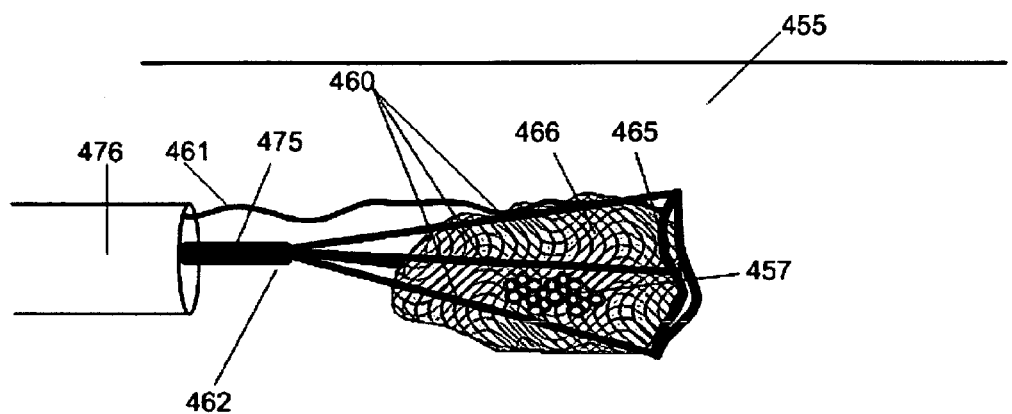
FIG. 4B illustrates an alternative embodiment according to the invention in a side view during a step in deployment of the device in a vessel of a subject, the vessel shown in cross-section.

FIG. 4A illustrates an embodiment of the present invention in which the collapsed filtration mesh 410 surrounds the tip of interventional catheter 425, after being pushed forward from the interior of guide catheter 426. This embodiment also includes semi-rigid struts 407. FIG. 4B illustrates the closure and retrieval of filtration mesh 466 in one embodiment of the present invention. Purse string 461 may be used to assist with the opening and collapse of struts 460, which differentially move at their vertex, which extends from interventional catheter 462. Once collapsed, the apparatus may be withdrawn through guide catheter 476. Alternatively, if the mesh 466, ring 465 and struts 460 are too large, or too full of filtered debris 457, they may be retracted through the incision following the removal of guide catheter 476.

Figure 4C:
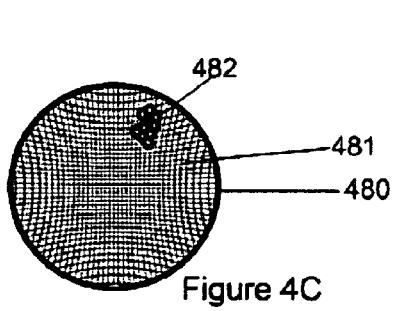
FIG. 4C illustrates an end view of an embodiment according to the invention during a step in deployment of the device.
Figure 4D:
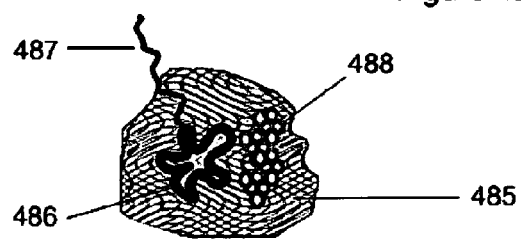
FIG. 4D illustrates an end view of an embodiment according to the invention during a later step in deployment of the device.

FIG. 4C illustrates mesh 481 and perimeter ring 480 along an end view, with trapped methacrylate or fat debris 482. FIG. 4D illustrates the same embodiment after purse string 487 has been pulled, closing perimeter ring 486, and trapping within mesh 485 debris 488.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. Such modifications and changes do not depart from the true spirit and scope of the present invention, which is set forth in the following claims.

We claim as our invention:

1. A filter system for removal of embolic particles from a blood vessel of a subject, the embolic particles having a particle size, the system comprising:
    an elongate interventional vascular catheter having a lumen and a distal end, the distal end of the catheter configured to advance distally within the blood vessel;
    an intravascular filter having a small profile configuration and a large profile configuration, the filter comprising a plurality of filtration elements;
    the filter in the small profile configuration being advanceable from within the lumen of the catheter and configured to deploy within the blood vessel of the subject by expansion of the filter from the small profile configuration to the large profile configuration;
    the filter in the large profile configuration having a plurality of openings defined between adjacent filter elements, the openings oriented so that bloodflow along the blood vessel from upstream of the filter passes through the openings when the filter is deployed in the blood vessel, the openings being larger than the particle size; and
    means, connected to the plurality of filter elements, for applying an electrostatic charge to the filtration element when the filter is deployed within the blood vessel so that the embolic particles electrostatically adhere to said filtration elements such that a substantial number of the adhered embolic particles remain in contact with the filtration element so as to be removed from the subject by removal of said filter from the blood vessel of the subject.

2. The filter system as set forth in claim 1 wherein said embolic particles comprise lipids.

3. The filter system as set forth in claim 1 wherein said embolic particles comprise methacrylate.

4. The filter system as set forth in claim 1 wherein said filtration element further comprises one or more struts.

5. The filter system as set forth in claim 1 wherein said filtration element further comprises one or more purse strings.

6. The filter system as set forth in claim 1 wherein said system may be retrieved from the vessel of a subject in a minimally invasive percutaneous manner.

7. The filter system as set forth in claim 1 wherein said filtration element further comprises a mesh having pores comprising a diameter of 10-30 microns.

8. The filter system as set forth in claim 1 wherein said system is constructed to selectively entrap small particle embolic material while permitting flow of non-selected particles therethrough.

9. The filter system as set forth in claim 1 wherein said embolic particles comprise fat.

10. A filter system for removal of embolic particles from a blood vessel of a subject, the system comprising:
    an elongate interventional vascular catheter having a lumen and a distal end, the distal end of the catheter configured to advance distally within the blood vessel;
    an intravascular filter having a small profile configuration and a large profile configuration, the filter comprising a plurality of filtration elements configured for deployment within a blood vessel of the subject by expansion from the small profile configuration to the large profile configuration, wherein the filter in the large profile configuration has a plurality of openings defined between adjacent filtration elements, the filtration elements comprising interleaved positive charge filtration elements and negative charge filtration elements;
    an anode coupled with a cathode, the anode electrically coupled with the positive charge filtration elements and the cathode electrically coupled with the negative charge filtration elements, the anode and cathode configured to maintain an electrical charge therebetween so as to impose an electrostatic charge between the adjacent filtration elements when the filter is deployed within the blood vessel of the subject such that embolic particles are captured between said positive charge filtration elements and the negative charge filtration elements, and such that a substantial number of the captured embolic particles are removed from the subject when said filter is removed from the subject.

11. The filter system as set forth in claim 10 wherein said embolic particles comprise lipids.

12. The filter system as set forth in claim 10 wherein said embolic particles comprise methacrylate.

13. The filter system as set forth in claim 10 wherein said filtration element further comprises a mesh.

14. The filter system as set forth in claim 10 wherein said filtration element further comprises one or more struts.

15. The filter system as set forth in claim 10 wherein said filtration element further comprises one or more purse strings.

16. The filter system as set forth in claim 10 wherein said system further comprises a delivery configuration and a deployed configuration whereby said system may be delivered and deployed in a minimally invasive percutaneous manner.

17. The filter system as set forth in claim 10 wherein said system may be retrieved from the vessel of a subject in a minimally invasive percutaneous manner.

18. The filter system as set forth in claim 10 wherein said filtration element further comprises a mesh having pores comprising a diameter of 10-30 microns.

19. The filter system as set forth in claim 10 wherein said system is constructed to selectively entrap small particle embolic material while permitting flow of non-selected particles therethrough.

20. The filter system as set forth in claim 10 wherein said embolic particles comprise fat.

21. The filter system as set forth in claim 10, the embolic particles having a size, wherein the openings are oriented so that bloodflow along the blood vessel from upstream of the filter passes through the openings when the filter is deployed in the blood vessel, the openings being larger than the particle size.

* * * * *